(12) United States Patent
Grodzins et al.

(10) Patent No.: US 6,765,986 B2
(45) Date of Patent: Jul. 20, 2004

(54) X-RAY FLUORESCENCE ANALYZER

(75) Inventors: Lee Grodzins, Lexington, MA (US); Hal Grodzins, Bedford, MA (US)

(73) Assignee: Niton Corporation, Billerica, MA (US)

( * ) Notice: Subject to any disclaimer, the term of this patent is extended or adjusted under 35 U.S.C. 154(b) by 0 days.

(21) Appl. No.: 10/067,683

(22) Filed: Feb. 4, 2002

(65) Prior Publication Data

US 2002/0154732 A1 Oct. 24, 2002

Related U.S. Application Data

(60) Provisional application No. 60/267,298, filed on Feb. 8, 2001.

(51) Int. Cl.$^7$ ............................................. G01N 23/223
(52) U.S. Cl. .............................. 378/46; 378/45; 378/48; 378/49
(58) Field of Search ............................... 378/44, 45, 46, 378/48, 49, 119, 136, 207, 210; 250/308, 370.06

(56) References Cited

U.S. PATENT DOCUMENTS

| | | | | |
|---|---|---|---|---|
| 3,843,881 A | | 10/1974 | Barton et al. ............... | 250/269 |
| 3,889,113 A | * | 6/1975 | Rhodes ......................... | 378/45 |
| 3,953,127 A | * | 4/1976 | Ahlquist et al. ............. | 356/339 |
| 4,063,089 A | * | 12/1977 | Gamba ......................... | 378/45 |
| 4,283,625 A | * | 8/1981 | King ............................. | 378/45 |
| 4,362,935 A | | 12/1982 | Clark ........................... | 378/48 |
| 5,062,127 A | * | 10/1991 | Sayama et al. .............. | 378/45 |
| 5,274,688 A | | 12/1993 | Grodzins ..................... | 378/45 |
| 5,497,407 A | * | 3/1996 | Komatsu et al. ............. | 378/45 |
| 6,563,902 B2 | * | 5/2003 | Takahashi ..................... | 378/49 |

FOREIGN PATENT DOCUMENTS

JP 63271147 11/1988

OTHER PUBLICATIONS

Sackett et al. EPA Method 6200 and Field Portable X–ray Fluorescence, 1998, http://www.niton.com/martin.html.*
EPA Method 6200 (May 1998) http://www.niton.com/meth6200.html.*
NEWMOA Technology Review Committee Advisory Opinion Innovative Technology: X–Ray Fluorescence Field Analysis (Sep. 21, 1999), wysiwyg://77/http://www.epa.gov/region01/steward/ceit/xrfweb.html.*
Mann, K.S., et al., "Determination of L–shell X–ray Production Cross–Sections in Holmium by 10–40 keV Photons," Pramana J. Phys., vol. 37, No. 3, Sep. 1991, pp. 293–302.
International Search Report, dated Aug. 1, 2002, received Aug. 5, 2002.

* cited by examiner

*Primary Examiner*—Edward J. Glick
*Assistant Examiner*—Courtney Thomas
(74) *Attorney, Agent, or Firm*—Bromberg & Sunstein LLP

(57) ABSTRACT

An x-ray fluorescence analyzer and method. The analyzer and method use a single radio-active source, such as, $^{241}$Am to determine the composition of a metal alloy or precious metal. The method compensates for Rayleigh scattering by first determining a scaling factor using a particular energy line in the spectrum of the test material and comparing that line to the same energy line for a pure metal. Based on the scaling factor the energy spectrum for the pure is compensated and then subtracted from the energy spectrum of the test material at discrete points.

27 Claims, 7 Drawing Sheets

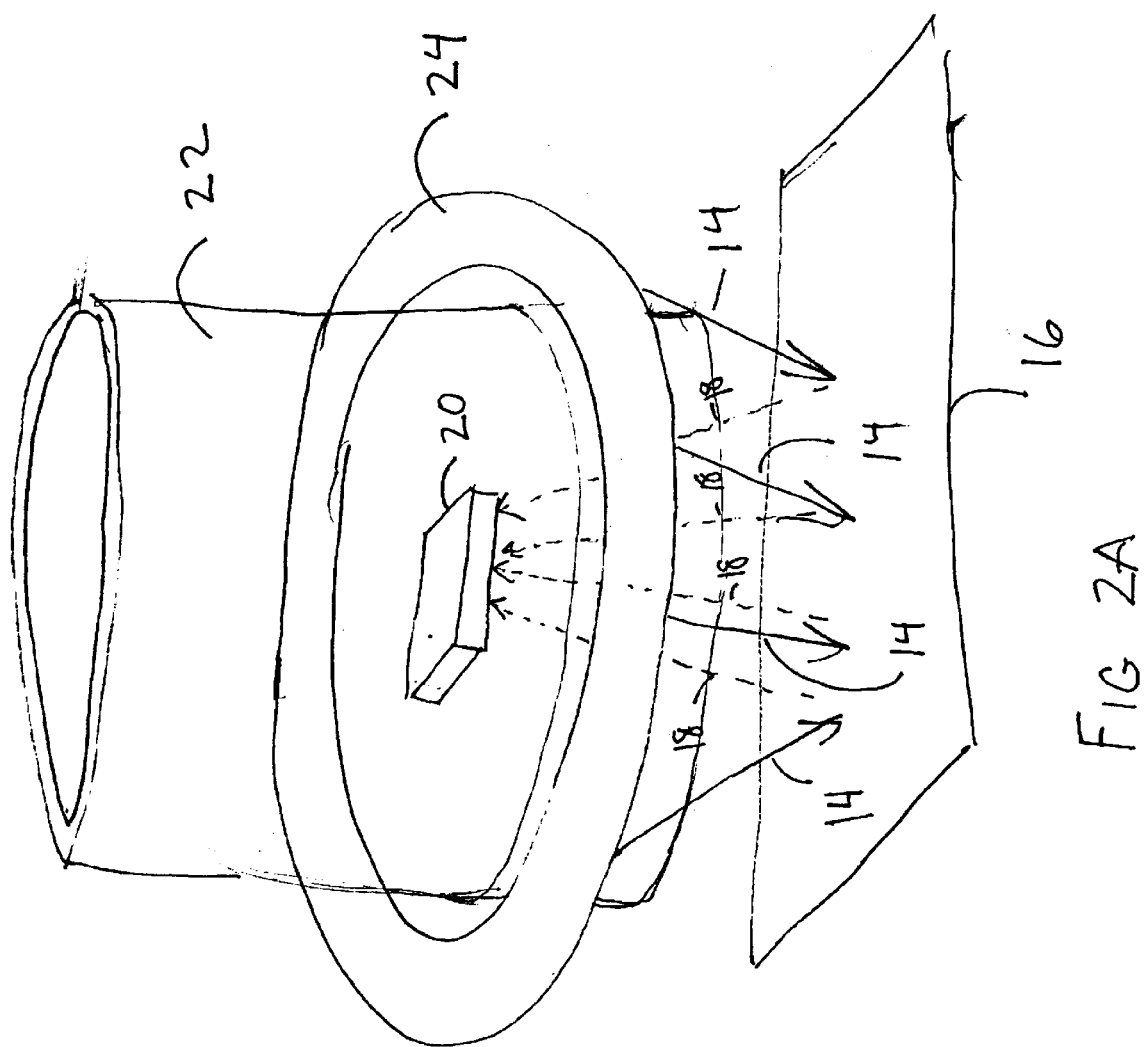

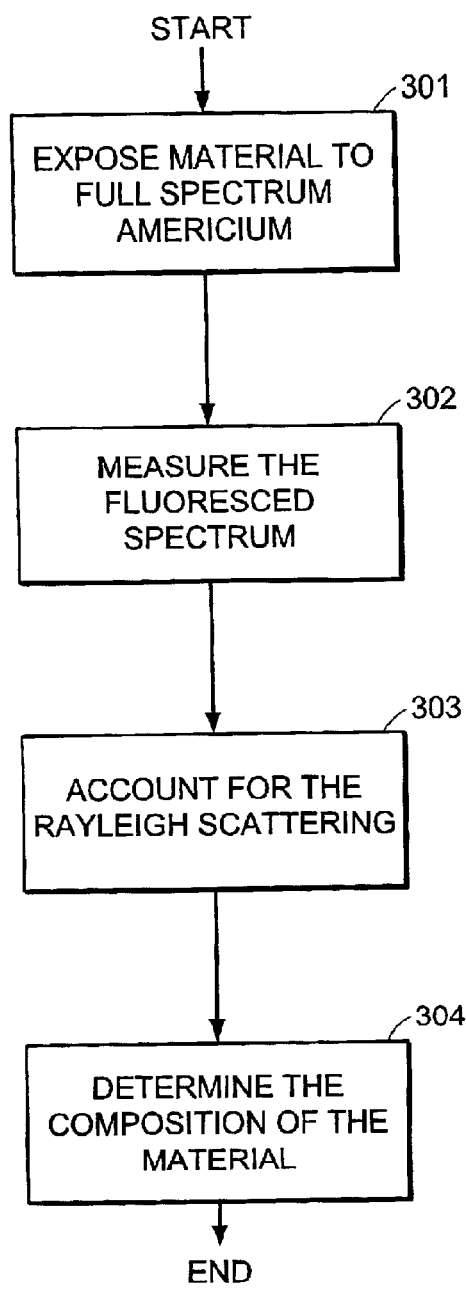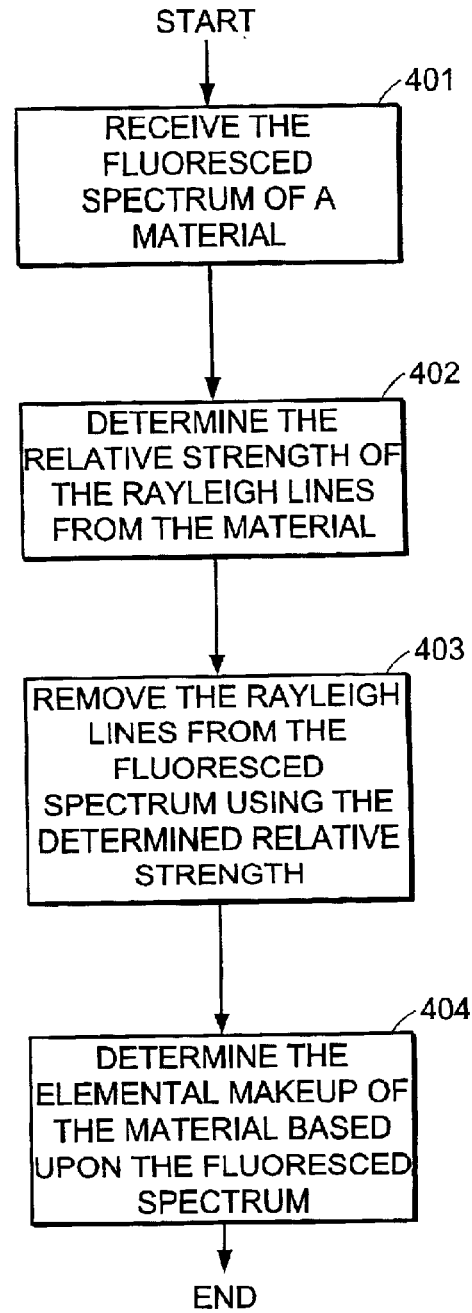
FIG. 3
FIG. 4

X-RAY FLUORESCENCE ANALYZER

PRIORITY

The present application claims priority from U.S. Provisional Patent Application No. 60/267,298 entitled "X-Ray Fluorescence Analyzer," which was filed on Feb. 8, 2001 which is incorporated by reference in its entirety.

TECHNICAL FIELD AND BACKGROUND ART

Quantitative analysis of metal alloys in the field is an essential component to such commercial applications as the sorting of recyclable scrap metal, on-site sample analysis in mining facilities, non-destructive testing in specialty metal manufacturing, and positive material inspection of alloys. X-Ray Fluorescence ("XRF") is the standard technique used to measure the composition of the major and minor elementary components with atomic number greater than about 20.

FIG. 1 is a prior art system that is used for measuring the composition of metal alloys and precious metals. As shown in FIG. 1, kilovolt photons 14 from a radioactive source 24, impinge on a target 16 whose elements are to be analyzed. In front of the radioactive source is a window 17, which is typically made out of stainless steel. The fluoresced x-rays 18 are detected in an energy-dispersing detector 20 connected to electronics 28. The detector 20 is shielded from the radiation of source 24 and from any ambient radiation by a shield 22. The incident photons 14 interact with the target 16 to produce the principal types of fluorescent radiation 18 including Compton scattering, Rayleigh scattering and photoelectric emission. Compton scattering produces a scattered x-ray with a lower energy than the incident x-ray; Rayleigh scattering produces an unchanged photon energy; and photoelectric emission, which occurs when an x-ray is absorbed by an element and x-rays characteristic of the element are emitted when the atom deexcites. The energy distribution of the fluorescent radiation is the sum of the characteristic x-rays from the target elements, the scattered radiation, and background radiations unconnected with the presence of the target. The energies of the gamma rays and x-rays emitted in the decays of $^{241}$Am, $^{55}$Fe and $^{109}$Cd are given in Table I.

TABLE 1

| Energy of XRF Radioisotopes | | | |
|---|---|---|---|
| Isotope | Half-Life | Energy, keV | Identification |
| $^{55}$Fe | 2.73 years | 5.9 keV | $K_\alpha$ |
| | | 6.5 keV | $K_\alpha$ |
| $^{109}$Cd | 462 days | 22.2 keV | $K_\alpha$ |
| | | 25 keV | $K_\beta$ |
| | | 88 keV | Gamma |
| $^{241}$Am | 433 years | 13.9 keV | $L_\alpha$ |
| | | 17.8 keV | $L_\beta$ |
| | | 20.8 keV | $L_\gamma$ |

TABLE 1-continued

| Energy of XRF Radioisotopes | | | |
|---|---|---|---|
| Isotope | Half-Life | Energy, keV | Identification |
| | | 26.4 keV | Gamma |
| | | 59.5 keV | Gamma |

In order to analyze alloys and precious metals, XRF instruments must have high efficiency for exciting and detecting x-rays whose energies range from a few keV to approximately 35 keV. To attain such sensitivity for alloy analysis, the XRF instruments now deployed in the field, including those made by Niton Corporation, use several x-ray sources, each with an energy spectrum most sensitive to specific regions of the periodic table.

In the prior art XRF analyzers, the multiple radioactive sources are used in sequence and are changed by a changing module 32 so that each x-ray source is sequentially exposed to the material being analyzed. The three standard x-ray sources are $^{241}$Am, $^{109}$Cd and $^{55}$Fe, though sometimes $^{253}$Gd or $^{239}$Pu are substituted for $^{241}$Am The 59.5 keV gamma rays of $^{241}$Am makes that source sensitive to elements in the tin region (Z=50), and efficiently covers the range of elements from rhodium (Z=45) to the rare-earth thulium (Z=69). A $^{109}$Cd source is a strong emitter of 22.2 keV x-rays that are efficient for exciting the K x-ray spectra of elements from chromium (Z=25) to ruthenium (Z=44) as well as the L x-ray spectra of heavier elements from tungsten (Z=74) through uranium (Z=92); the 88 keV gamma ray is too weak for quick-time measurements. The 5.9 keV x-ray of $^{55}$Fe is effective for exciting the elements titanium (Z=22), and vanadium (Z=23). The relative sensitivities of the three sources for measuring elements are given in Table 2.

TABLE 2

| Relative Effectiveness of $^{55}$Fe, $^{109}$Cd, and $^{241}$Am Sources for XRF of an Iron Matrix | | | | | | | | | | |
|---|---|---|---|---|---|---|---|---|---|---|
| | Ti | Cr | Fe | Zn | W(L) | Pb(L) | Zr | Mo | Ag | Ba |
| $^{55}$Fe | 0.07 | 0.025 | | | | | | | | |
| $^{109}$Cd | .014 | 0.034 | 0.08 | 0.05 | 0.06 | 0.16 | 0.68 | 1.2 | | |
| $^{241}$Am, 59 keV | 0.001 | 0.002 | 0.005 | 0.003 | 0.004 | 0.01 | 0.05 | 0.08 | 0.21 | 1.0 |

All commercially available alloy analyzers use $^{109}$Cd sources as the primary source with $^{55}$Fe used to increase the sensitivity to the lightest elements and $^{241}$Am to analyze the elements in the tin region.

Multi-source instruments have several drawbacks. One drawback is cost. The individual radioactive sources are expensive and adding additional radioactive sources increases the cost proportionally. Second, when testing is performed on a material, the radioactive sources are used sequentially to minimize interference. Using the sources sequentially is very time consuming. Third, in order to use the source in a sequential manner, each source requires a source-changing mechanism, increasing the cost, size and complexity of the analyzer. Fourth, the multi-source system has issues of normalization and mechanical reproducibility.

Although a single source instrument would provide distinct advantages and overcome the inherent problems described above, certain prohibitions have caused the reliance on multi-source instruments. First, there is no known single radioactive source that provides a usable energy spectrum when used with the prior art XRF analysis methods. For example, an $^{241}$Am source has a spectrum with strong monoenergetic photons emitted in the range from 13.9 keV to 26.4 keV and previous analytic methods were unable to quantify this region due to the interfering Rayleigh and Compton scattering intensities that depended on the material being analysed.

SUMMARY OF THE INVENTION

In a first embodiment of the invention there is provided a device for photon fluorescence. The device includes a single radioactive source, such as $^{241}$Am. Both the emitted x-rays and gamma rays are used to determine the composition of a test material, such as a metal alloy or a precious metal that contains trace elements. An energy detector is used for receiving the fluoresced x-rays and gamma rays from the test material. The energy detector passes a signal to electronics for processing. The electronics process the signal and determine the composition of the test material based in part on the fluoresced x-rays and gamma rays. The electronics compensate for interfering Rayleigh and Compton scattering peaks by first choosing a Rayleigh scattered peak in a region of the spectrum that does not interfere with any fluoresced x-ray from the metal sample. This is the reference peak for the spectrum. For metal samples, the intensity of Rayleigh scattering through 180° is sufficiently independent of Z that the intensity of the reference peak determines the intensity of all the other Rayleigh scattered lines. Specifically, the Rayleigh scattered spectrum from a typical metal such as iron is stored in the device's computer. The intensity of the reference line in the sample spectrum is compared to the intensity of the reference line in the stored spectrum and the ratio is applied to the stored spectrum, which is then subtracted out of the sample spectrum. In this way, one accounts for the interfering Rayleigh peaks in the measured sample spectrum. The intensity of Compton scattering in the 12 keV to 20 keV range is low enough, from metals heavier than titanium, that they can be taken into account as well from the reference spectrum. The invention is illustrated with the use of $^{241}$Am since this source is traditionally used as a source of only 59.5 keV gamma rays. The technique can be usefully employed with other sources, for example $^{239}$Pu. If that source is used with a beryllium exit window so that the L lines are used and not absorbed, then the 12.6 keV $L_\alpha$ line is the appropriate normalizing Rayleigh peak.

The device further includes a shield for the radioactive source. The shield isolates the detector from direct exposure to the x-rays and gamma rays of the radioactive source so that the detector mainly receives the fluoresced radiation from the test material. The shield surrounds the radioactive source except in the direction of the test material. A source backing may be selected such as Rhodium so that the radioactive material interacts with the source backing to produce photons which combine with the x-rays and gamma rays of the source to increase the fluoresced radiation of the test material.

In certain embodiments, the shape of the shield is ring-shaped and holds the radioactive material wherein the energy detector resides inside of the ring. In another embodiment, the radioactive material is in the center and the energy detector is effectively ring-shaped around the source.

BRIEF DESCRIPTION OF THE DRAWINGS

The foregoing features of the invention will be more readily understood by reference to the following detailed description, taken with reference to the accompanying drawings, in which:

FIG. 2A is a diagram in which the radiation source is ring-shaped.

FIG. 3 is a flow chart of the steps used to determine the composition of a material using the full spectrum of Americium.

FIG. 4 is a flow chart of the steps used to remove the Rayleigh lines from the fluoresced spectrum of the material.

DETAILED DESCRIPTION OF SPECIFIC EMBODIMENTS

In the following specification, the probabilities for detecting the characteristic x-rays, Compton scattering and Rayleigh scattering are given by the following equations. Backscattered geometry is assumed and geometrical effects and detector efficiencies are subsumed in the K constants. It is further assumed that the analyzed samples are thick enough so that exponential terms that depend on the source thickness are negligible. It should be understood by one of ordinary skill in the art that the presentation of these equations is for clarity and that a more complete version of the equations, without assumptions, may suitably be used without straying from the intent of the invention. Characteristic x-ray intensity (equation 1):

$$I(K_Z) < \frac{\mu_{p.e.}(Z, E_{inc})}{\mu_{total}(Z_{matrix}, E_{inc}) + \mu_{total}(Z_{matrix}, E_K)}$$

Compton intensity (equation 2):

$$I(E_{Compton}) < \frac{\mu_{Compton}(Z_{matrix}, E_{inc})}{\mu_{total}(Z_{matrix}, E_{inc}) + \mu_{total}(Z_{matrix}, E_C)}$$

Rayleigh intensity (equation 3):

$$I(E_{Rayleigh}) < \frac{\mu_{Rayleigh}(Z_{matrix}, E_{inc})}{\mu_{total}(Z_{matrix}, E_{inc}) + \mu_{total}(Z_{matrix}, E_{inc})}$$

where $\mu_{p.e.}$ is the mass absorption coefficient for the photoelectric effect where $\mu_{Rayleigh}$ is the mass absorption coefficient for the Rayleigh scattering where $\mu_{Compton}$ is the mass absorption coefficient for Compton scattering.

and where $\mu_{total}$ is the total mass absorption coefficient.

Figure 1:
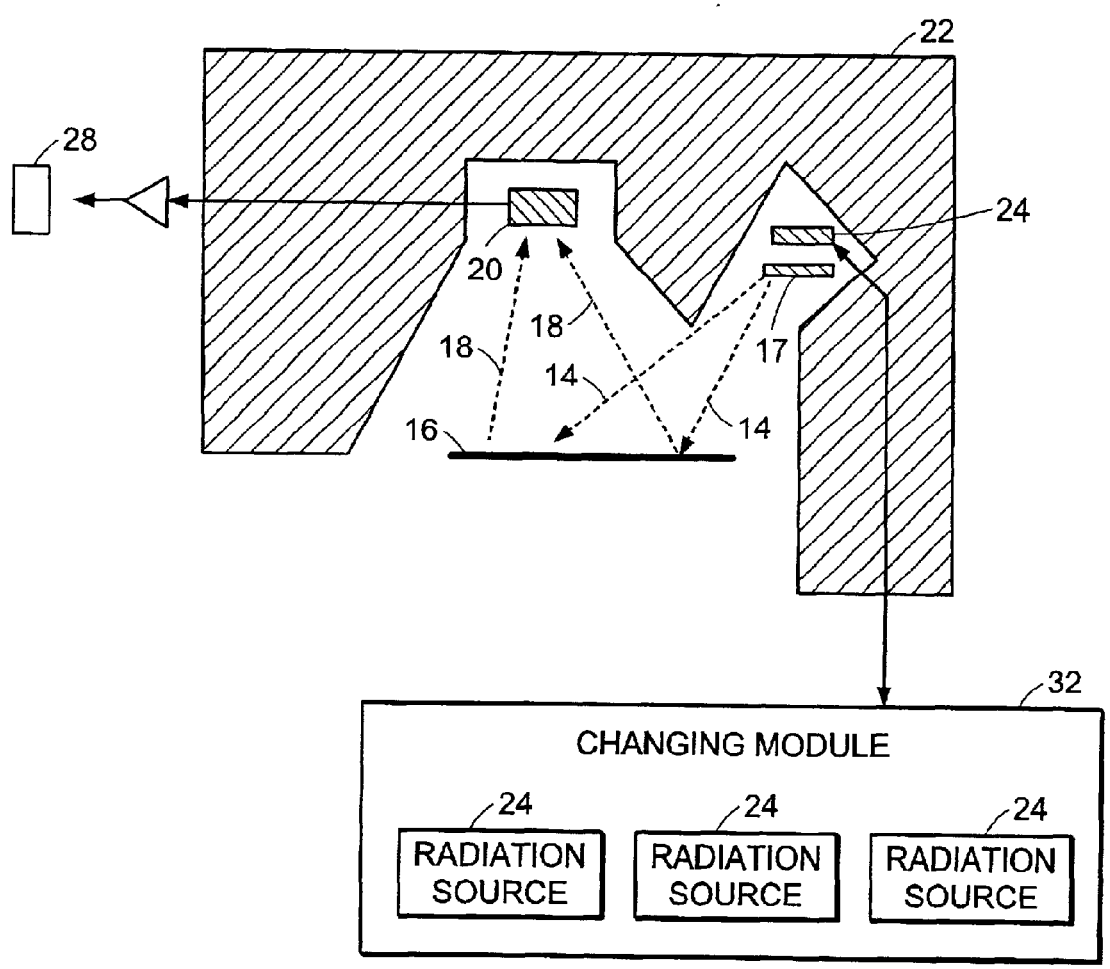
FIG. 1 is a diagram of a prior art x-ray fluorescence analyzer which uses three radioactive sources and provides a changing mechanism for the sources.
Figure 2:
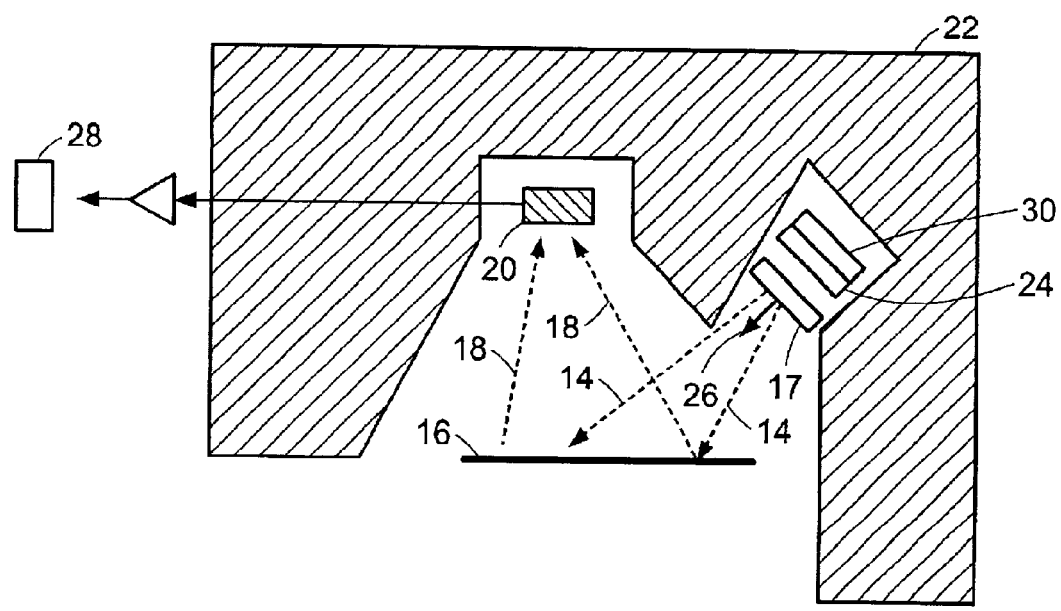
FIG. 2 is a diagram of one embodiment of an apparatus for determining the composition of an alloy or precious metal that uses only one radioactive source.

FIG. 2 is a diagram of a system which uses a single radiation source for determining the composition of a target sample, such as, an alloy or precious metal. Unlike prior art systems, the present invention as embodied has only one radioactive source and therefore does not require the changing module of FIG. 1. In the preferred embodiment the system is sized to be a hand-held, portable x-ray fluorescent instrument. The system includes a radioactive source that provides kilovolt photons which are directed onto the target sample. The kilovolt photons 14 contact the target sample and produce fluoresced x-rays 18. The x-rays are detected in a high-resolution, energy-dispersing detector 20 connected to electronics 28 including a processor. The electronics, after receiving the signals that are representative of the full fluoresced x-ray spectrum from the detector, perform a pre-processing step on the received signals. During the pre-processing step, the background noise due to Rayleigh and Compton scattering is removed. From these pre-processed signals, the composition of the target sample can be determined using techniques known to those of ordinary skill in the art.

The preferred source 24 is $^{241}$Am. $^{241}$Am emits an alpha particle to decay to $^{237}$Np. The 59.5 keV gamma ray is the most intense photon but the $L_\alpha$, $L_\beta$, and $L_\gamma$ x-rays of Np, at 13.945 keV, 17.40 keV and 20.8 keV respectively, are also of a strength to be used for analysis. The $^{241}$Am is sealed in front (in the direction of the target sample) with a beryllium window that allows the L x-rays to emerge with negligible absorption. Between the $^{241}$Am source and the shield is a disc of rhodium 30 that is fluoresced by the 59.5 keV gamma rays that are emitted away from the target sample (in the direction of the rhodium). It should be understood that although the shape of the rhodium is a disk in the above recited embodiment, the rhodium may take other shapes. The rhodium emits x-rays of 20.07 keV to 22.7 keV and the x-rays that are emitted in the direction of the target sample pass through the americium source with little attenuation and add to the effective source strength. The backing is not limited to the preferred rhodium; other elements, in particular, silver or barium may be as effective or even more effective for particular situations. To utilize the full spectrum from $^{241}$Am, the source area is made appropriately large enough to minimize self-absorption and the source material is sealed in the front by an appropriately thin window such as beryllium 17, rather than absorbing stainless steel, which is typically used. The radiation from source 24 is shielded from the detector 20 and the ambient environment by an appropriate shield 22 which absorbs the radiation along all sides except in the direction of the target sample. It should be understood by one of ordinary skill in the art that the configuration of the shield 22, the detector 20, and the source 24 may take various configurations and is not limited to the configuration as shown in FIG. 2 without deviating from the scope of this invention. For example, in certain embodiments, the $^{241}$Am radioactive source is held in a ring shaped holder and the energy detector resides within the ring.

The XRF spectrum is analyzed according to the method described below and shown in FIG. 3. The target sample is exposed to not just the 59 keV gamma ray of $^{241}$Americium as was done in the prior art, but to the full spectrum of radiation produced by the $^{241}$Am x-ray source (Step 301). The fluoresced spectrum is then measured via a radiation detector/sensor (Step 302). The sensor converts the radiation into an electromagnetic signal, which is forwarded to a processor. The processor then performs preprocessing on the signal in order to compensate for Rayleigh and Compton scattering. (Step 303). The intensity of the 13.9 keV line from the Rayleigh scattering of the 13.9 keV $L_\alpha$ line of $^{241}$Am is used to eliminate the background spectrum over the entire energy range from 12 keV to 20 keV. This is achieved by determining the relative intensity at 13.9 keV for the target sample as compared to the intensity at 13.9 keV for a pure metal such as iron, and then normalizing the entire spectrum proportionately. If the spectrum contains sufficient strength in the titanium peak at 4.5 keV, then an additional (small) correction may be made to account for additional background in the 16.5 keV to 18 keV region to account for Compton scattering. From the fluoresced x-ray spectrum, the composition of the material is determined using techniques know to those of ordinary skill in the art (Step 304).

In comparison to the $^{55}$Fe, $^{109}$Cd, $^{241}$Am combination of the prior art systems, the effectiveness of the full spectrum of $^{241}$Am is shown in the table below.

TABLE I

Comparison of the Effectiveness of Different Sources for XRF

|  | Ti | Cr | Fe | Zn | W(L) | Pb(L) | Zr | Mo | Ag | Ba |
|---|---|---|---|---|---|---|---|---|---|---|
| $^{55}$Fe | 0.07 | 0.025 |  |  |  |  |  |  |  |  |
| $^{109}$Cd | .014 | 0.034 | 0.08 | 0.05 | 0.06 | 0.16 | 0.68 | 1.2 |  |  |
| $^{241}$Am, 59 | 0.001 | 0.002 | 0.005 | 0.003 | 0.004 | 0.01 | 0.05 | 0.08 | 0.21 | 1.0 |
| $^{241}$Am, all | 0.011 | 0.023 | 0.05 | 0.04 | 0.04 | 0.09 | 0.11 | 0.17 | 0.25 | 1.0 |

The values in the tables are the probabilities of photo-emission of characteristic x-rays calculated from Equations 3 using theoretical photon interaction probabilities provided in NIST tables. The effectiveness of the $^{241}$Am(all) source is comparable to the combination of $^{109}$Cd and $^{241}$Am (59 keV only) except in the Zr—Mo region. In that region, the sensitivity of the $^{241}$Am(all) source is lower, but it is still adequate for measuring the concentration of Zr or Mo in alloys. $^{241}$Am(all) is about a factor of 6 less sensitive to Ti than is a $^{55}$Fe source, but that is partly compensated by using a stronger $^{241}$Am source than would be used $^{55}$Fe$^{109}$Cd$^{241}$Am, 59 keV combination.

Figure 5:
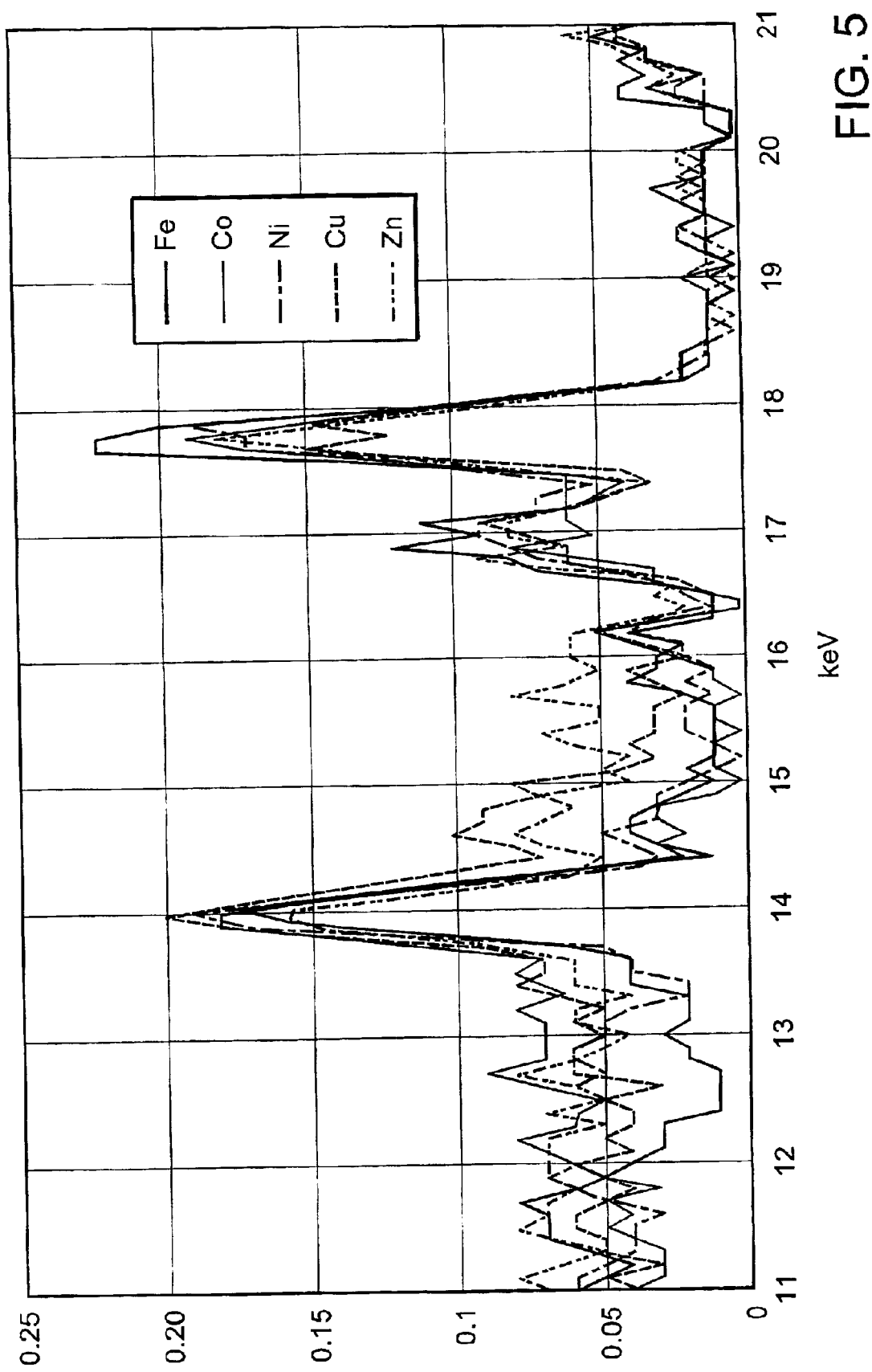
FIG. 5 is a graph showing the Rayleigh scattering for various materials.

The intensity of the background spectra from the Rayleigh scattering of the L x-ray lines which are in the 10 keV to 20 keV range for an $^{241}$Am source is almost independent of the composition of alloys. This is true for all alloys made primarily from metals heavier than titanium, and the background spectra is only weakly dependent on the composition of titanium alloys. FIG. 5 is a graph showing the XRF spectrum in the energy region from 10 keV to 22 keV obtained from quite pure metal targets; Fe, Co, Ni, Cu and Zn. (It is seen that the intensity of the Compton peaks in FIG. 5 is negligible). The background spectra over the region from 12 keV to 20 keV are nearly identical. Based upon this, the strength of the 13.9 keV Rayleigh peak may be used as a normalizer to subtract out the background for the entire region. The 13.9 keV line is particularly useful since K x-rays that overlap with it are from strontium, which is not a normal component of alloys.

The methodology used by the processor for compensating for the Rayleigh scattering is now described and shown in the flowchart of FIG. 4. The fluoresced spectrum is received by the processor (Step 401). The value for the 13.9 keV is determined from the signal produced by the target sample. By knowing the Rayleigh scattering intensity level at 13.9 keV based upon a pure metal standard such as the spectra shown in FIG. 5, a normalization factor is determined (Step 402). The normalization factor provides the proportion between the 13.9 keV line from the target sample and the ideal 13.9 keV line from the pure metal standard. The normalization factor is then applied to the entire spectrum of the pure metal standard (Step 403). The normalized pure metal standard spectrum is then subtracted from the full spectrum of the target sample at discrete points, thereby removing the Rayleigh scattering from the spectrum of the target sample. The discrete points may be every point within the spectrum or at the Rayleigh lines at 17.74 keV (strong), 16.8 keV (weak) and 20.8 keV (weak). These energy lines are chosen since they interfere with the x-ray lines from three elements that do occur in metal alloys: Molybdenum (17.4 keV to 20 keV), Niobium (16.5 keV to 19 keV) and zirconium (15.7 keV to 18 keV). From the spectrum of the target sample free from interfering Rayleigh lines, the individual elements which are present in the target sample are then determined using well known techniques (Step 404), generally called Fundamental Parameter Analysis. It should be understood by one of ordinary skill in the art that the above described method may be embodied in a computer program product for use with a computer processor in which matrix algebra and other mathematical and computer science techniques may be applied which would allow for increased computational speed without deviating from the spirit of the above described method.

Figure 6:
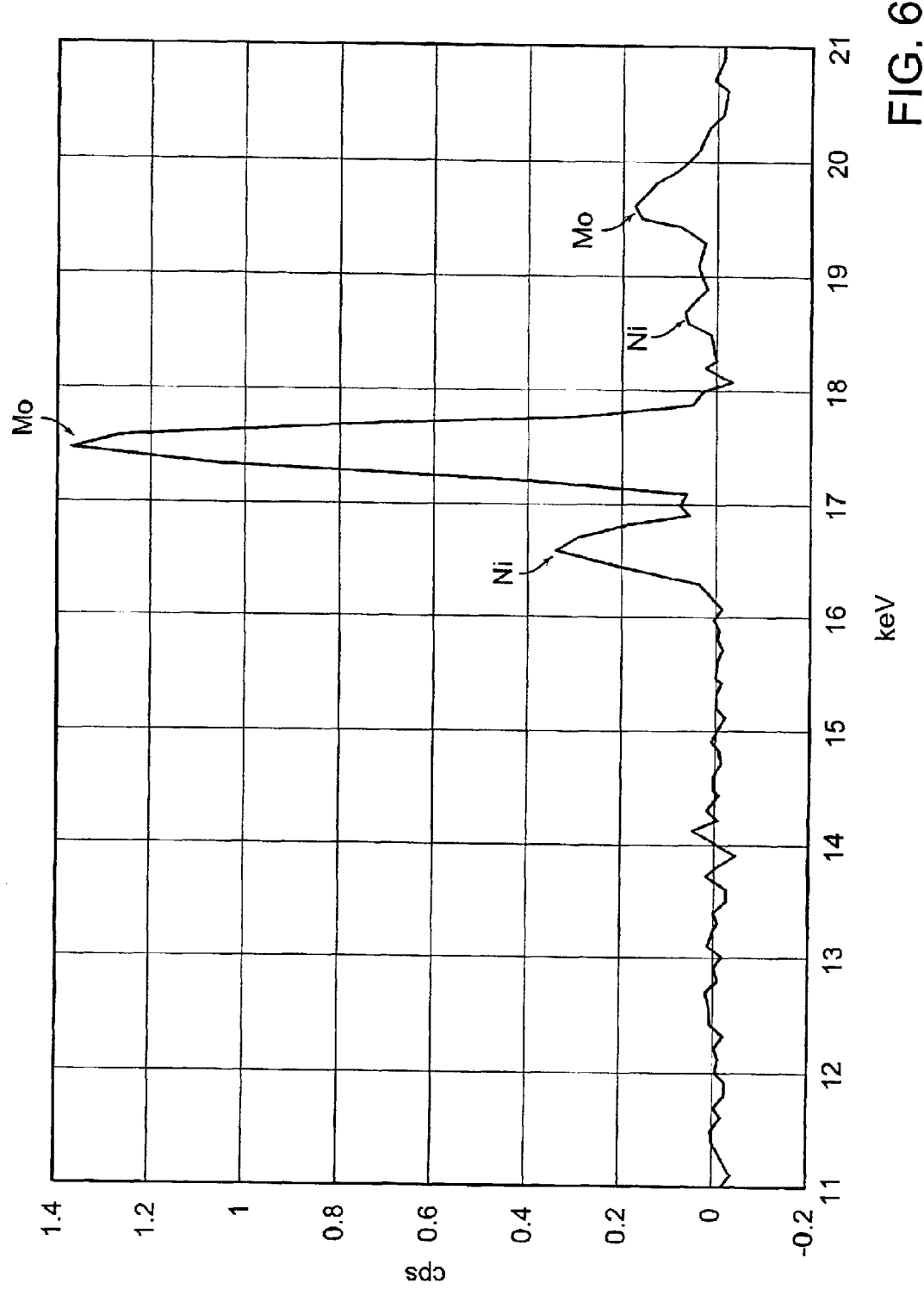
FIG. 6 is a graph showing a fluoresced spectrum with the background Rayleigh and Compton scattering removed.

FIG. 6 is a graph which shows the normalized spectra of FIG. 5 in which the Rayleigh background has been subtracted using only the 13.9 keV line from an iron spectrum for normalization FIG. 6 shows the spectrum from a steel alloy, 20CB3 in which the only observed structure after subtraction comes from the 0.51% niobium and the 2.1% molybdenum in the alloy.

To enhance the $^{241}$Am emissions a source backing 30 (referring to FIG. 2), such as rhodium, that is fluoresced by the 59.5 keV line is used. In one embodiment of the present invention, the cover of $^{241}$Am source 24 is thin and the $^{241}$Am source itself has minimal self-absorption of its L x-rays. Rhodium is strongly fluoresced by the 59.5 keV gamma rays of $^{241}$Am, yielding K x-rays of 20.07, 20.2, and 22.7 keV; the 20.2 keV line being the strongest.

The strength of the rhodium x-rays 26 at the sample will be at least 15% of the strength of the 59.5 keV line and will therefore be about equal to the strength of the $L_\gamma$ line at 20.8 keV, doubling its effectiveness for fluorescing the sample. It should be noted that for some purposes the surrounding material around the source may be more than one element, either as a compound or layered.

Figure 7:
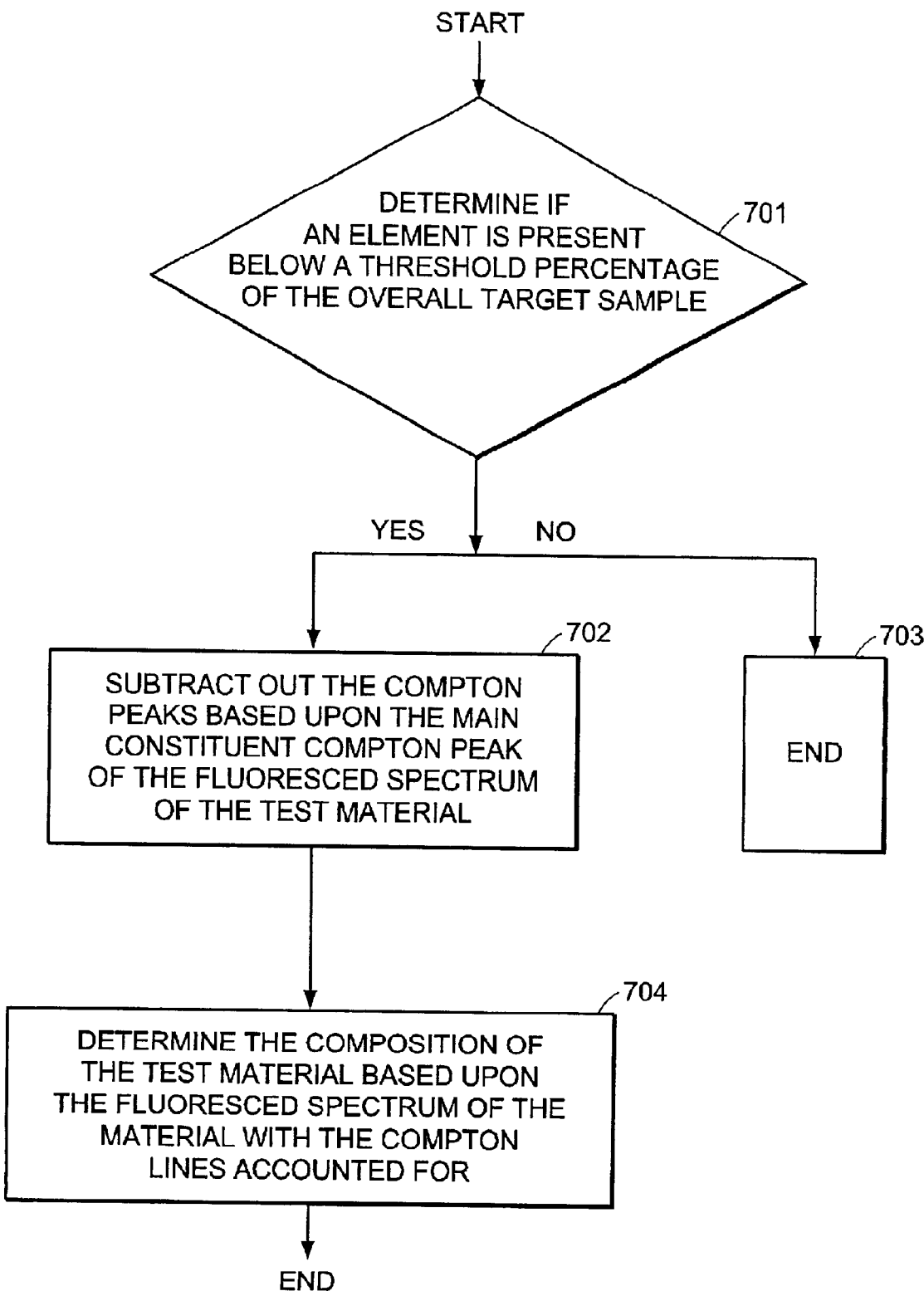
FIG. 7 is a flow chart of the steps used to remove the Compton Scattering lines from the fluoresced spectrum of the material.

The method may be further refined, as shown in the flowchart of FIG. 7, to account for the Compton scattering such as occurs with a titanium based alloy. First, it is determined if elements, such as, Mo, Nb or Zr are present within the alloy or precious metal at levels at or below a threshold, for example, approximately 0.5% by weight (Step 701). If the elements are present at levels below the threshold, then the Compton scattering is accounted for by subtracting out the Compton peaks in order to provide a more accurate measurement (Step 702). The strength of the main constituent peak (e.g. the titanium peak at 4.5 keV for titanium alloys) is used to make a first order estimate of the strengths of the Compton peaks from the L lines of the Am source. This value is then subtracted from the spectrum in order to obtain more sensitive values for the elements (Mo, Nb, and Zr). If the elements are not present at or below the threshold, the computation will end and the output will be the composition values that were previously determined (Step 703). After the Compton peaks are subtracted out, a further analysis is performed to determine the percentages of the elements in the test material (Step 704).

In an alternative embodiment, the disclosed method for determining the composition of a test material may be implemented as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a compute program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention. These and other obvious modifications are intended to be covered by the appended claims.

What is claimed is:

1. A device for analyzing a test material with respect to the presence of trace quantities of atoms in the range of atomic number at least between 45 and 69, and, at the same time, atoms in the range of atomic number at least between 22 and 44, the device comprising:

one and only one radioactive source emitting radiation due simultaneously to x-ray emission and to gamma emission due to radioactive decay, the x-ray emission giving rise to a Rayleigh scattering line that may overlap with characteristic x-rays of the test material, the Rayleigh line characterized by an intensity;

a window interposed between the radioactive source and the test material for allowing irradiation of the test material by both x-ray emission and gamma emission;

an energy-dispersive detector for receiving fluoresced radiation from the test material and generating a signal based on detected intensity as a function of energy; and electronics coupled to the energy-dispersive detector for generating a spectrum of detected intensity as a function of energy based on the signal, the spectrum scaled on the basis of the intensity of the Rayleigh line, the electronics including a processor for determining the composition of elements within the test material based at least upon the fluoresced radiation.

2. A device according to claim 1, wherein the processor further estimates the strength of a Compton scattering peak due to an x-ray line of the radioactive source and subtracts it from the spectrum.

3. A device according to claim 1, wherein the electronics compensate for Rayleigh scattering by normalizing the spectrum produced by the fluoresced radiation using a pure metal standard spectrum.

4. A device according to claim 1 further comprising:

a shield for the radio active source isolating the detector from direct exposure to the x-rays and gamma rays of the radioactive source.

5. A device according to claim 4, wherein the shield surrounds the radioactive source except in the direction of the test material.

6. A device according to claim 4, wherein the radioactive material is rhodium.

7. A device according to claim 1, wherein the source is $^{241}$Am.

8. A device according to claim 7, wherein both the 59.5 keV and the 26.4 keV photons of the $^{241}$Am source are used in determining the composition of the test material.

9. A device according to claim 7, wherein the 59.5 keV and the 26.4 keV gamma rays along with the L x-rays of the $^{241}$Am source are used in determining the composition of the test material.

10. A device according to claim 1, wherein the source is $^{239}$Pu.

11. A device according to claim 1, wherein the test material is a metal alloy.

12. A device according to claim 1, wherein the test material is a precious metal.

13. A device according to claim 1, wherein the radiation of the radioactive source interacts with a reactive material to produce photons which combine with the radiation of the source to increase the fluoresced radiation of the test material.

14. A device according to claim 1, wherein the radioactive source is ring shaped forming a ring and the energy detector resides within the ring.

15. A method for analyzing a test material, the method comprising:

providing a single radioactive source emitting both x-rays and gamma rays, wherein the single radioactive material is $^{241}$Am;

exposing the test material to the x-rays and gamma rays of the radioactive material;

receiving fluoresced radiation into an energy-dispersive detector;

generating a spectrum scaled according to an intensity of a Rayleigh scattering line associated with an x-ray line of the source; and determining the composition of the test material for multiple elements in a processor based in part upon the received fluoresced radiation spectrum from the x-rays and gamma rays of the $^{241}$Am.

16. A method according to claim 15 further comprising: subtracting Compton and Rayleigh scattering lines associated with the source from the spectrum.

17. A method according to claim 15 wherein in determining the composition, a resulting spectrum of the fluoresced x-rays and gamma rays is analyzed to identify spectral peaks representative of elements found in the test material.

18. A method according to claim 15 further comprising: accounting for Rayleigh scattering by subtracting a scaled pure-metal fluoresced spectrum from the fluoresced spectrum of the test material.

19. A method according to claim 18 wherein the pure-metal fluoresced spectrum is scaled based upon a factor which is the ratio of a spectral line of the pure-metal fluoresced spectrum and a spectral line of the fluoresced spectrum of the test material resulting from the source.

20. A method according to claim 15, wherein the test material is a metal alloy.

21. A method according to claim 15, wherein the test material is substantially a metal.

22. A method according to claim 21, wherein the metal is a precious metal.

23. A method according to claim 15, further comprising:

exposing the radio active source with a material fluoresced by photons emitted from the radioactive source which increases the fluoresced x-rays and gamma rays received by the energy detector.

24. A computer program product readable by a computer processor and having computer code thereon, for analyzing a test material with respect to the presence of trace quantities of atoms in the range of atomic number at least between 45 and 69, and, at the same time, atoms in the range of atomic number at least between 22 and 44, the computer code comprising:

computer code for generating a compensated energy spectrum of fluoresced radiation of the test material which is exposed to one and only one radioactive source wherein radiation from the radioactive source gives rise to a Rayleigh scattering line, the Rayleigh scattering line characterized by an intensity wherein the compensated energy spectrum is scaled on the basis of the intensity of the Rayleigh line; and computer code for determining the composition of the test material for multiple elements based upon the compensated energy spectrum.

25. A computer program product according to claim 24, wherein the computer code for generating includes:

computer code for calculating a normalization factor using the line of the source;

computer code for applying the normalization factor to an energy spectrum of a pure material; and computer code for subtracting the energy spectrum of the pure material from the energy spectrum of the test material.

26. The computer program product according to claim 25, wherein the computer code for calculating a normalization factor includes: computer code for comparing the Rayleigh line of the source to a comparable Rayleigh line of the pure material.

27. The computer program product according to claim 25, further comprising:

computer code for estimating the strength of a Compton scattering peak due to an x-ray line of the radioactive source; and subtracting the Compton scattering peak from the compensated energy spectrum of the test material.

* * * * *